United States Patent

Seiler et al.

[11] Patent Number: 5,804,817
[45] Date of Patent: Sep. 8, 1998

[54] SENSOR DEVICE FOR DETECTING THE DEGREE OF WETTING AND/OR CONTAMINATION OF WINDOWS, ESPECIALLY WINDSHIELDS OF MOTOR VEHICLES

[75] Inventors: Hartmut Seiler, Baden-Baden; Rainer Pientka, Achern; Horst Fedter, Bühlertal, all of Germany

[73] Assignee: Robert Bosch GmbH, Stuttgart, Germany

[21] Appl. No.: 491,931

[22] PCT Filed: Dec. 28, 1993

[86] PCT No.: PCT/DE93/01245

§ 371 Date: Jul. 13, 1995

§ 102(e) Date: Jul. 13, 1995

[87] PCT Pub. No.: WO94/15819

PCT Pub. Date: Jul. 21, 1994

[30] Foreign Application Priority Data

Jan. 13, 1993 [DE] Germany .......................... 43 00 655.8
Dec. 20, 1993 [DE] Germany .......................... 43 43 474.6

[51] Int. Cl.⁶ ........................................... G01N 21/17
[52] U.S. Cl. ........................ 250/227.25; 250/577; 318/483
[58] Field of Search .................... 250/227.24, 227.25, 250/577; 340/602; 318/483

[56] References Cited

U.S. PATENT DOCUMENTS 4,652,745  3/1987  Zanardelli .................... 250/227.25

FOREIGN PATENT DOCUMENTS 0254636  1/1988  European Pat. Off. .
0299606  1/1989  European Pat. Off. .
0562275  9/1993  European Pat. Off. .
3823300  8/1989  Germany .
4202121  12/1992  Germany .

*Primary Examiner*—Stephone Allen
*Attorney, Agent, or Firm*—Spencer & Frank

[57] ABSTRACT

A sensor device for detecting the degree of wetting and/or contamination of windows, especially windshields of motor vehicles, which device has a radiation source (12) emitting a radiation into the window (10) from the inside of the window (10), and a radiation measuring device detecting the radiation reflected many times by total reflection in the window (10) between outer surface (17) and inner surface (18). A heating device (33) is arranged on at least one contact surface between the sensor device and the window (10) or in the window. As a result, the measurement path (19) of the window (10) is deliberately heated with a low energy requirement, so that no measurement impairment is to be feared as a result of condensation on the inner surface (18) of the window and a mirrored reflection surface on this inside is not necessary.

15 Claims, 2 Drawing Sheets

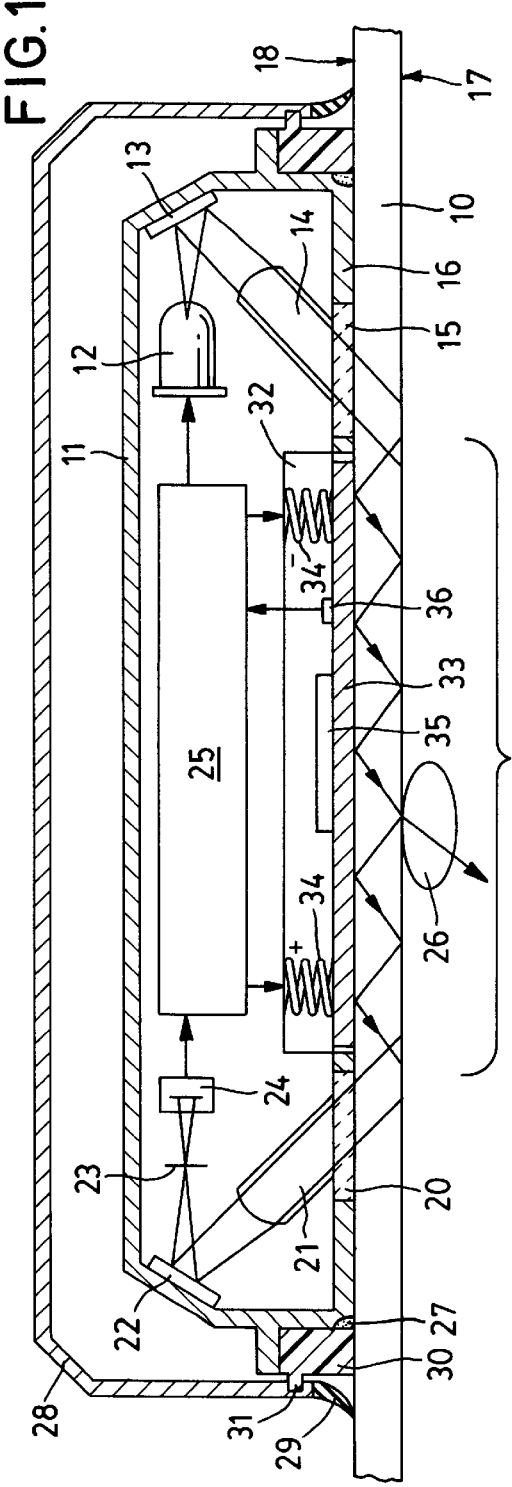
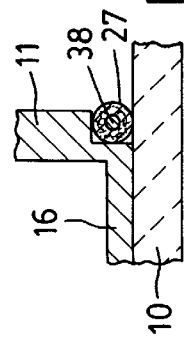
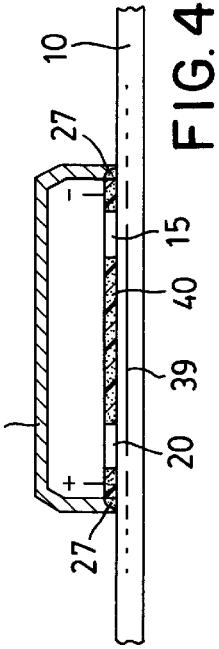

SENSOR DEVICE FOR DETECTING THE DEGREE OF WETTING AND/OR CONTAMINATION OF WINDOWS, ESPECIALLY WINDSHIELDS OF MOTOR VEHICLES

BACKGROUND OF THE INVENTION

Prior Art

The invention relates to a sensor device for detecting the degree of wetting and/or contamination of windows, especially windshields of motor vehicles, of the type having a radiation source emitting a radiation into the window from the inside of the window, a radiation measuring device detecting the radiation reflected by total reflection in the window between an outer surface and an inner surface of the window along a measurement path, and a heating device.

DE-C 38 23 300 and DE-C 40 06 174 disclose sensor devices of this type which operate according to the principle of attenuated total reflection. For this purpose, the radiation emitted by a radiation source is reflected many times (total reflection) at the window outer and inner surface along a measurement path and is then detected by a radiation measuring device. Dirt particles or raindrops on the outside prevent the total reflection and therefore attenuate the reflection in the window interior, which results in a signal attenuation which can be detected by the radiation measuring device. Below a predeterminable limiting value, means for window cleaning, for example, are then automatically switched on.

In the case of a sensor device of this type, the problem can arise that condensation is formed on the window inside, that is to say between the sensor device and the window, as a result of large temperature differences between the inside and outside of the window. This condensation likewise leads to a falsification of the measurement result, since the total reflection is now impaired by the condensation formation on the inside of the window. The known sensor devices therefore have a reflection layer with a high-gloss surface, which is applied to the inside of the window in a sealing manner with an optical intermediate medium, in order to prevent the penetration of air and condensation. The high-gloss surface ensures total reflection. However, the production of such reflection layers coupled in a sealing manner to the inside of the window is very complicated and increases the cost of the production of the sensor device. Furthermore, this reflection layer can clearly be detected from outside and is optically disturbingly noticeable to the observer.

In addition, the known sensor devices are provided with a heating device in order to achieve heating up of the entire sensor device to, for example, 40° C. This is used, for example, to thaw a snow covering on the outside of the window in the region of the sensor device and to evaporate partially formed condensation in the event of the encapsulation of the reflection layer with the high-gloss surface not being completely airtight. Despite the heating device, the high-gloss surface which is applied as tightly as possible to the inside of the window is therefore necessary. Furthermore, as a result of the heating-up of the entire sensor device, a relatively high electrical energy requirement arises and the components must be designed accordingly.

SUMMARY AND ADVANTAGES OF THE INVENTION

A sensor device for detecting the degree of wetting and/or contamination of windows, especially windshields of motor vehicles, having: a radiation source emitting a radiation into the window from the inside of the window, a radiation measuring device detecting the radiation reflected by total reflection in the window between an outer surface and an inner surface of the window along a measurement path, and a heating device; and wherein the heating device is disposed on the contact surface between the sensor device and the window or in the window adjacent the measurement path to directly and deliberately heat the measurement path.

In contrast to known arrangement, the sensor arrangement according to the invention as described above has the advantage that an additional reflection surface with a high-gloss surface on the inside of the window can be completely omitted, since the formation of condensation can be prevented by means of direct targeted heating of the inside of the window in the region of the measurement path, so that the total reflection on the inside of the window itself remains ensured. Since now only a very small area is heated, the heat energy needed is very small. The sensor device itself is not heated up unnecessarily. In addition, the expenditure for the optical coupling of a mirrored reflection surface and a pretreatment of the window can be omitted. The measurement path and thus the sensor device is now hardly visible from the outside, so that the optical impression is improved.

Advantageous further developments and improvements of the basic sensor arrangement according to the invention are possible and are disclosed and discussed below.

The heating device is designed in the simplest case as a heating plate or heating film resting on the window in the region of the measurement path. This heating plate or this heating film is intended to have a surface finish which, on the one hand, does not interfere with the total reflection and, on the other hand, produces the desired thermal contact with the window. However, in principle no particular requirements are necessary for the contact on the window, so that both simple and cost-effective mounting and also cost-effective production are possible.

An advantageous refinement relates to the heating plate or heating film. Openings, for example holes of defined size and at defined spacing (perforation), make it possible to quickly dry out any condensation present on the internal measurement path.

A simple and favorable construction results from designing at least one part of the base, resting on the window, of a housing of the sensor device as a heating plate. In this case, the sensor device or this housing needs to be fastened only to the window, for example by sticking on. In this arrangement, a design in which the heating plate is held resiliently on the window by spring means is favorable to the thermal contact. In this arrangement, two springs can be provided as spring means, which are designed simultaneously as current supply leads for the heating plate.

For heating the heating plate or the heating film, a heating wire is preferably integrated in the latter. However, it is also possible to produce the heating plate from a conductive plastic, especially one having a PTC characteristic, and to feed a heating current directly through it. A further possibility consists in arranging heating elements, such as PTC elements, heating resistors or the like, on the heating plate.

A further expedient possibility consists in fitting a heating wire arrangement in or on the window as a heating device, for example in the fashion of the known heatable rear windshield. In principle, this heating wire arrangement need only be arranged in the region of the measurement path, but it can of course also extend over the entire window.

Finally, there exists a further expedient possibility for the design of a heating device in that this is arranged as a heating wire in the seal between the sensor arrangement and the window.

In order to achieve defined relationships independent of the respective outside or inside temperature, a temperature sensor for the heating device and a temperature control device are provided in an advantageous way, in order to keep the measurement path at constant temperature.

BRIEF DESCRIPTION OF THE DRAWINGS

Exemplary embodiments of the invention are shown in the drawing and described in more detail in the following description. FIG. 1 shows a first exemplary embodiment of a sensor device according to the invention with a heating plate resting resiliently on the inside of the window in a vertical sectional representation, FIG. 2 shows the heating plate resting on the window in accordance with FIG. 1 in a top view, FIG. 3 shows a detailed representation of a heatable seal, FIG. 4 shows a housing for the sensor device with a heatable baseplate which can be rested on the window.

DETAILED OF THE EXEMPLARY EMBODIMENTS

Figure 5:
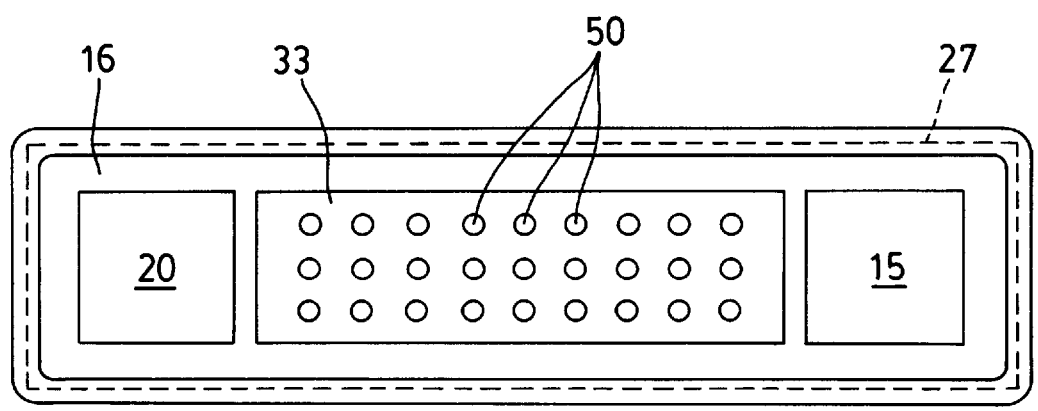
FIG. 5 shows a configuration of the heating plate or heating film, resting on the window, in accordance with FIG. 1 in a top view.

The sensor device, shown in the figures, for detecting the degree of wetting and/or contamination is bonded to the inside of a glass window 10, which can, for example, be the windshield of a motor vehicle. Of course, an application is also possible in the case of other window panes or transparent windows, which may also consist, for example, of a plastic material.

A light-emitting diode 12 is located as radiation source in a housing 11 which can be rested on the window 10. The emitted radiation is deflected at a first deflection mirror 13 on the inside of the housing and passes at an angle into the window 10 via a first prism 14 and a transparent optical region 15 in the housing base 16 resting on the window 10. By virtue of the prism 14, the radiation is aligned in parallel. The angle is selected such that total reflection occurs at the outer surface 17 and the inner surface 18 in the window 10. After a plurality of reflections in a measurement path 19 of the window 10, the radiation then emerges once more at a second transparent optical region 20 in the housing base 16. By means of a prism 21 arranged thereon, the radiation is focussed such that it has its focal point, after the deflection by a second deflection mirror 22, in the plane of a diaphragm 23 which is disposed downstream in the beam path. A photodiode 24, arranged downstream of the focal point, forms the essential part of a radiation measuring device and measures the intensity of the incident radiation. The evaluation of the radiation received in the photodiode 24 and the control of the light-emitting diode 12 are carried out via an electronic control and measuring circuit 25.

If there are water droplets 26 or dirt particles on the window 10 in the region of the measurement path 19, the total reflection is then disturbed, and part of the radiation emerges from the window, as a result of which the intensity of the radiation received in the photodiode 24 is attenuated. This signal attenuation is evaluated in the control and measuring circuit 25 in such a manner that, below a limiting value, which can be fixed, of the intensity, a switching process is carried out as a result of which, for example, the windshield wiper of the vehicle is switched on or a soft top and/or side windows can be closed. An evaluation circuit which is suitable for this is described, for example, in DE-C 23 54 100 or in the prior art specified at the outset.

The housing 11 is sealed off at the periphery of its bearing surface on the window 10 by means of a toroidal cord seal 27. Furthermore, to protect the housing 11, an even larger protective housing 28 is placed over the housing 11, and is sealed off with respect to the window 10 by means of a lip seal 29. An elastic connecting element 30 on the outer periphery of the housing 11 has a latching projection 31 which, when the protective housing 28 is placed over, latches into a corresponding cutout in the same.

In the region of the measurement path 19, in a cutout 32 in the housing base 16, a heating plate 33 is provided which is pressed, by means of two springs 34 in the case of a sensor device resting on the window 10, against this window 10. The surface structure, which is in contact with the window 10, of this heating plate 33 is finished such that, on the one hand, the total reflection is not disturbed and, on the other hand, a good thermal contact with the window is produced. A suitable surface structure provides, for example, pimples which act as spacers. To heat the heating plate 33, this plate is provided with a heating element 35 on the side facing away from the window. This heating element 35—there can also be a plurality—is, for example, a heating resistor or a PTC element. The two current supply leads for the heating element 35 are provided via the springs 34 via the control and measuring circuit 25 or directly to the heating element 35. Said control and measuring circuit 25 is furthermore fed the signal of a temperature sensor 36 arranged on the heating plate 3. As a result, temperature control of the heating plate 33 to an approximately constant temperature of, for example, 60° C., irrespective of the outside and inside temperature of the window 10, is possible. This prevents the formation of condensation, which could falsify the measurement result, on the inside of the window 10 in the region of the measurement path 19.

In a simpler embodiment, a temperature sensor 36 can also be omitted, and the heating element 35 is supplied by a current which is constant but which could, for example, be set as a function of the outside temperature. Apart from the prevention of the formation of condensation, streaks or fogging on the window can also be evaporated away more rapidly by means of such a heating plate 33.

FIG. 2 shows the housing base 16, surrounded by the toroidal cord seal 27, in a top view. Between the two transparent optical regions 15 and 20, the cutout 32 and a heating plate 41 arranged therein are shown. Differing from FIG. 1, no external heating element 35 is provided for heating the heating plate 41, rather the heating plate 41 has in the interior a heating wire 37 which is connected to the two springs 34 serving as current supply leads.

In a more simple modification of the sensor device according to FIGS. 1 and 2, the heating plate 33 or 41 can also be arranged rigidly in the housing base 16, leaving out the springs 34. It is likewise possible to fit a heating foil in the region of the measurement path 19 on the housing base 16 or to apply it to the window 10 at the corresponding location.

According to the representation in FIG. 3, the toroidal cord seal 27 can also contain a heating wire 38 and can be heated, so that the enclosed measurement path 19 is likewise heated. The heated toroidal cord seal 27 can be used as an additional heater or, in a very simple design, even as the sole heater.

In the case of the exemplary embodiment shown in FIG. 4, a housing base 40 consists of conductive plastic with a PTC characteristic. A separate heating plate can therefore be omitted. A heating voltage is applied to the housing base 40, as a result of which the housing base 40 is heated in the desired manner. Furthermore, a heating wire 39 is integrated in the window 10 in FIG. 4. This heating wire 39 or several such heating wires in this case cover at least the measurement path 19, but can also extend out beyond the sensor device. Such heating wires, integrated in a window, are realized, for example, in normal heated rear windshields. Instead of the heating wire 39, corresponding heating tracks can also be evaporated onto the window. Such a heating by means of a heating wire 39 can be used as additional heating of the measurement path 19, but sole heating of the latter by means of this heating wire 39 is also possible. A combination with the previously described exemplary embodiments is likewise possible.

FIG. 5 shows an advantageous configuration either of the heating plate/heating film 33 shown in FIG. 1 or the heating plate/heating film 41 shown in FIG. 2 or the housing base 40, shown in FIG. 4 and designed as a heater. The reference symbol 33 used in FIG. 5 can therefore be replaced by the reference symbol 41 or by the reference symbol 40. The heating plate/heating film 33, 41, which is arranged between the two transparent optical regions 15, 20, or the housing base 40 has openings 50. The openings 50 are, for example, bored holes which have a defined diameter and preferably a defined spacing from one another. The openings 50 can be designated perforations. Instead of the bored holes with a circular cross section, shown in FIG. 5, any other conceivable shapes are suitable. It is essential that the openings 50 make possible rapid drying-off of any condensation present on the inner measurement path, which corresponds to the inner window surface.

We claim:

1. Sensor device for detecting the degree of wetting and/or contamination of windows, having: a radiation source emitting a radiation into the window from the inside of the window, a radiation measuring device detecting the radiation reflected by total reflection in the window between an outer surface and an inner surface of the window along a measurement path, and a heating device; and, wherein the heating device is disposed on the contact surface between the sensor device and the window or in the window adjacent the measurement path to directly and deliberately heat the measurement path.

2. The sensor device as claimed in claim 1, wherein the heating device is arranged on the window and is a heating plate or heating film.

3. The sensor device as claimed in claim 2, wherein the heating plate or heating film is a part of a base, resting on the window (10), of a housing of the sensor device.

4. The sensor device as claimed in claim 3, wherein the heating plate is held resiliently on the window by elastic means.

5. The sensor device as claimed in claim 4, wherein two springs are provided as the elastic means and as current supply leads for the heating plate.

6. The sensor device as claimed in claim 2, wherein a heating wire is provided in the heating plate or heating film.

7. The sensor device as claimed in claim 2, wherein the heating plate or heating film consists of a conductive plastic.

8. The sensor device as claimed in claim 2, wherein heating elements are arranged on the heating plate.

9. The sensor device as claimed in claim 1, wherein the heating device arranged in or on the window is a heating wire arrangement.

10. The sensor device as claimed in claim 1, wherein a temperature sensor for the heating device is provided on the heating device and is connected to a temperature control device for the heating device.

11. The sensor device as claimed in claim 2 wherein the heating plate or heating film has a plurality to openings.

12. The sensor device as claimed in claim 11 wherein the opening are holes having a defined size and at a defined spacing.

13. The sensor device as claimed in claim 3 wherein the part, constituting a heating plate or heating film and resting on the window, of the base of the housing of the sensor device has a plurality to openings.

14. The sensor device as claimed in claim 13 wherein the opening are holes having a defined size and a defined spacing.

15. The sensor device as claimed in claim 7 wherein the conductive plastic has a positive temperature coefficient characteristic.

* * * * *